(12) United States Patent
Hill et al.

(10) Patent No.: US 8,067,334 B2
(45) Date of Patent: Nov. 29, 2011

(54) SELECTIVE HYDROGENATION CATALYST

(75) Inventors: Thomas Hill, Ludwigshafen (DE); Hermann Petersen, Grunstadt (DE); Germain Kons, Mannheim (DE); Henrik Junicke, Mannheim (DE)

(73) Assignee: BASF SE, Ludwigshafen (DE)

( * ) Notice: Subject to any disclaimer, the term of this patent is extended or adjusted under 35 U.S.C. 154(b) by 832 days.

(21) Appl. No.: 11/577,140

(22) PCT Filed: Oct. 13, 2005

(86) PCT No.: PCT/EP2005/011026
§ 371 (c)(1), (2), (4) Date: Apr. 12, 2007

(87) PCT Pub. No.: WO2006/040159
PCT Pub. Date: Apr. 20, 2006

(65) Prior Publication Data
US 2009/0030250 A1 Jan. 29, 2009

(30) Foreign Application Priority Data
Oct. 13, 2004 (DE) .................. 10 2004 059 282

(51) Int. Cl.
*B01J 23/66* (2006.01)

(52) U.S. Cl. ........ 502/330; 502/325; 502/332; 502/333; 502/334; 502/339; 585/258; 585/259; 585/260; 585/271; 585/273

(58) Field of Classification Search .................. 585/260, 585/258, 259, 271, 273; 502/325, 330, 332, 502/333, 334, 339
See application file for complete search history.

(56) References Cited

U.S. PATENT DOCUMENTS

| | | | | |
|---|---|---|---|---|
| 4,404,124 A * | 9/1983 | Johnson et al. | ............... | 502/201 |
| 4,409,410 A * | 10/1983 | Cosyns et al. | ................ | 585/259 |
| 4,421,676 A * | 12/1983 | Puskas et al. | ................ | 502/185 |
| 5,648,576 A | 7/1997 | Than et al. | | |
| 5,889,187 A | 3/1999 | Than et al. | | |
| 6,054,409 A | 4/2000 | Thanh et al. | | |
| 6,066,589 A * | 5/2000 | Malentacchi et al. | ........ | 502/185 |
| 6,197,721 B1 * | 3/2001 | Didillon et al. | ................ | 502/326 |
| 6,350,717 B1 * | 2/2002 | Frenzel et al. | ................ | 502/330 |
| 6,437,206 B1 * | 8/2002 | Meyer et al. | ................... | 585/260 |
| 6,602,821 B2 * | 8/2003 | Petit-Clair et al. | ............ | 502/306 |
| 2002/0165092 A1 | 11/2002 | Zhang et al. | | |
| 2004/0192983 A1* | 9/2004 | Bergmeister et al. | ......... | 585/259 |

FOREIGN PATENT DOCUMENTS

| | | |
|---|---|---|
| DE | 3119850 | 2/1982 |
| EP | 0686615 | 12/1995 |
| EP | 0780155 | 6/1997 |
| EP | 0992284 | 4/2000 |
| WO | 2004074220 | 9/2004 |

OTHER PUBLICATIONS

Thiemann, et.al., "Nitric Acid, Nitrous Acid, and Nitrogen Oxides" in Ullmann's Encyclopedia of Industrial Chemistry, Wiley, published on-line Jun. 15, 2000.*

McCormick, et.al., "Drying" in Kirk-Othmer Encyclopedia of Chemical Technology, Wiley, published on-line Jan. 15, 2004.*

Delage, et al., "Highly dispersed Pd based catalysts for selective hydrogenation reactions," Studies in Surface Science and Catalysis, 130 (2000), p. 1019-1024.*

McCormick, et al., "Drying" in the Kirk-Othmer Encyclopedia of Chemical Technology, Wiley, published on-line Jun. 18, 2004, pp. 121-122.*

* cited by examiner

*Primary Examiner* — In Suk Bullock
*Assistant Examiner* — Bradley Etherton
(74) *Attorney, Agent, or Firm* — Connolly Bove Lodge & Hutz LLP

(57) ABSTRACT

A catalyst on an oxidic support and processes for selectively hydrogenating unsaturated compounds in hydrocarbon streams comprising them using these catalysts are described.

26 Claims, No Drawings

SELECTIVE HYDROGENATION CATALYST

This application is the National Phase of International Application No. PCT/EP2005/011026 filed on Oct. 13, 2005; and this application claims priority to Application No. 102004059282.9 filed in Germany on Oct. 13, 2004 under 35 U.S.C. §119; the entire contents of all are hereby incorporated by reference.

The present invention relates to hydrogenation catalysts which comprise metals of group VIII of the Periodic Table of the Elements on a support material, and to processes for selectively hydrogenating unsaturated compounds in hydrocarbon streams comprising them using these catalysts.

In refineries and petrochemical plants, hydrocarbon streams are obtained, stored and processed on a large scale. In these hydrocarbon streams, unsaturated compounds are frequently present, whose presence is well known to lead to problems, especially in the course of processing and/or storage, or are not the desired product of value and are therefore undesired components of the corresponding hydrocarbon streams.

Typically, the components to be hydrogenated in C3 streams are propyne (methylacetylene, MA) and propadiene (allene, PD).

In C4 streams, 1,3-butadiene can be the product of value. In this case, 1,3-butadiene is extracted and the remaining C4 cut, the raffinate I, has to be freed of butadiene traces by selective hydrogenation, by hydrogenating the butadiene selectively to butenes.

However, when no use for pure butadiene but a high demand for butenes exists, the high proportion of 1,3-butadiene from the crude C4 stream of the steamcracker can be hydrogenated selectively to butenes. In addition, 1,2-butadiene, butenyne (vinylacetylene), butyne (ethylacetylene) and traces of propadiene which has not been removed by distillation in this crude C4 cut can be hydrogenated.

For some subsequent processes (for example metathesis with ethene to propene), a high content of 2-butenes is required. Since the 2-butenes have a distinct thermodynamic preference over 1-butene at the reaction temperatures, they are generally obtained in excess in the hydrogenation. When, however, 1-butene is the product of value, special catalysts are consequently required to obtain predominantly 1-butene.

In general, it is therefore usually necessary to remove unsaturated compounds having triple bonds (alkynes) and/or diunsaturated compounds (dienes) and/or di- or polyunsaturated compounds (polyenes, allenes, alkynenes) and/or aromatic compounds having one or more unsaturated substituents (phenylalkenes and phenylalkynes) from hydrocarbon streams in order to obtain the desired products such as ethylene, propylene, 1-butene, isobutene, 1,3-butadiene, aromatics or carburetor fuel in the required quality. However, not every unsaturated compound is always an undesired component which has to be removed from the hydrocarbon stream in question. For example, 1,3-butadiene, as already mentioned above, is an undesired secondary component or the desired product of value depending on the application.

Undesired unsaturated compounds are removed from hydrocarbon streams comprising them frequently by selective hydrogenation of some or all of the undesired unsaturated compounds in the corresponding hydrocarbon stream, preferably by selective hydrogenation to nontroublesome, more highly saturated compounds and more preferably to the components of the hydrocarbon stream which constitute products of value. For example, propyne and propadiene in C3 streams are hydrogenated to propene and butyne in C4 streams is hydrogenated to butenes, vinylacetylene to 1,3-butadiene and/or 1,3-butadiene to butenes.

Typically, such undesired compounds have to be removed down to residual contents of a few ppm by weight. The ("over"-)hydrogenation to compounds which are more highly saturated than the desired product of value and/or the parallel hydrogenation of a product of value containing one or more multiple bonds to the corresponding more highly or fully saturated compound should, however, be avoided as far as possible owing to the associated loss of value. The selectivity of the hydrogenation of the undesired unsaturated compounds therefore has to be as high as possible. In addition, a sufficiently high activity of the catalyst and a long lifetime are desired in general. At the same time, the catalyst should as far as possible also not bring about any other undesired side reactions. For example, catalysis of the double bond isomerization of 1-butene to 2-butene should be avoided when 1-butene is the product of value.

Typically, supported noble metal catalysts are used for the hydrogenation, in which the noble metal is deposited on a catalyst support. Frequently, palladium is used as the noble metal, and the support is generally a porous inorganic oxide, for example siliceous earth, aluminum silicate, titanium dioxide, zirconium dioxide, zinc aluminate, zinc titanate and/or a mixture of such supports. Usually, the support material used is alumina.

EP 0 992 284 A2 describes catalysts for the selective hydrogenation of unsaturated compounds in hydrocarbon streams which consist of noble metal or noble metal compounds on a specific $Al_2O_3$ support, the catalyst being defined by a particular x-ray diffraction pattern. This x-ray diffraction pattern is determined predominantly by the support.

DE 31 19 850 A1 describes a process for selectively hydrogenating a diolefin in a hydrocarbon mixture having at least four carbon atoms which comprises an α-olefin, wherein a catalyst is used which simultaneously comprises palladium or a palladium compound and silver or a silver compound, and the palladium content of the catalyst is 0.05-0.5% by weight and the silver content 0.05-1% by weight.

EP 780 155 A1 describes a selective hydrogenation catalyst in which alumina in the α-modification is used as a support material. The supported catalyst is coated with the hydrogenation-active metals palladium and silver, the content of palladium being 0.01-0.5% by weight and the content of silver 0.001-0.1% by weight. At least 30% of the metal particles of the catalyst are palladium and/or silver. The ratio of palladium to silver is 0.33-2.50. In addition, 80% of the palladium and of the silver lie within a profile of the thickness of not more than 0.2 r.

EP 0 686 615 A1 relates to a supported catalyst which comprises α-alumina as the support material and palladium and silver as hydrogenation-active metals. The content of palladium is 0.01-0.5% by weight and the content of silver is 0.001-0.02% by weight. 80% of the palladium and of the silver lie within the profile of the thickness of 0.2 r, the ratio of palladium to silver being 2.50-20.

U.S. Pat. No. 4,404,124 relates to a supported catalyst comprising the support material α-alumina and the hydrogenation-active metals palladium and silver. The palladium content is 0.01-0.25% by weight, while the silver content is 0.02-0.05% by weight. This results in a ratio of palladium to silver of not more than 0.5. Moreover, the palladium is present in the shell of the catalyst material up to 300 μm, while the silver is present over the entire cross section of the catalyst material in at least 90% of the catalyst pellets.

US 2002/0165092 A1 relates to a supported catalyst composed of alumina, which comprises palladium and silver as the hydrogenating metal. The palladium content is 0.002-1.0% by weight. This results in a ratio of palladium to silver of 1-20. The silver and the palladium are present uniformly in the profile, the penetration depth into the profile being more than 300 µm. In preferred embodiments, the penetration depth of the palladium and of the silver is between 500 and 1000 µm.

The known catalysts generally have the disadvantage of too low an olefin selectivity and of marked green oil formation, the olefin selectivity referring to the Δolefins/Δalkynes ratio.

The demands on catalysts and processes for selectively hydrogenating undesired unsaturated compounds in hydrocarbon streams comprising them are rising constantly with regard to the reduction of the residual content of undesired unsaturated compounds after the hydrogenation and to the increase in the selectivity. Although the known processes and catalysts work at a very high technical level, they are still unsatisfactory in view of the rising demand. It is therefore an object of the present invention to find an improved catalyst and an improved process for the selective hydrogenation of unsaturated compounds in hydrocarbon streams comprising them, the focus being directed to the provision of catalysts having high hydrogenation activity, high olefin selectivity, especially high 1-butene selectivity in the case of C4 hydrogenation, and also low green oil formation and associated long lifetime. Especially in the case of hydrogenations of C4 streams, the catalysts should still have a low double bond isomerization tendency, so that there is no significant catalysis of the isomerization of 1-butene to 2-butene.

The achievement of this object starts from a catalyst which comprises at least one metal of group VIII of the Periodic Table of the Elements as a hydrogenating metal and additionally a promoter on an oxidic support.

In the inventive catalyst, at least 80% of the metal of group VIII of the Periodic Table of the Elements is present in substantially homogeneous distribution in a layer between the surface of the catalyst and a penetration depth which corresponds to not more than 80% of the radius of the catalyst, calculated from the surface of the catalyst, and the promoter is present in substantially homogeneous distribution over the entire cross section of the catalyst.

In a preferred embodiment, the catalyst has a diameter of from 2.5 to 10 mm, and at least 80% of the metal of group VIII of the Periodic Table of the Elements is present in substantially homogeneous distribution in a layer between the surface of the catalyst and a penetration depth of not more than 1000 µm, calculated from the surface of the catalyst, and the promoter is present in substantially homogeneous distribution over the entire cross section.

According to the invention, a catalyst is thus provided in which the metal of group VIII of the Periodic Table of the Elements forms a shell structure in the catalyst, while the promoter is saturated through.

The naming of the groups of the Periodic Table of the Elements is according to the CAS nomenclature (Chemical Abstracts Service).

The inventive catalyst has a diameter of from 2.5 to 10 mm. In preferred embodiments of the inventive catalyst, the diameter is from 2.5 to 5 mm, in particular from 2.5 to 3.5 mm.

In the inventive catalyst, at least 80%, preferably at least 90%, more preferably at least 95%, in particular at least 98%, especially 100%, of the metal of group VIII of the Periodic Table of the Elements is present in substantially homogeneous distribution in a layer between the surface of the catalyst and a penetration depth of not more than 1000 µm, calculated from the surface of the catalyst.

The inventive catalyst comprises a metal of group VIII of the Periodic Table of the Elements (Fe, Ru, Os, Co, Rh, Ir, Ni, Pd, Pt). In a preferred embodiment of the present invention, it is palladium.

The inventive catalyst further comprises at least one promoter. For example, this may be further metals of group VIII, IB and IIB of the Periodic Table of the Elements (Cu, Ag, Au, Zn, Cd, Hg). In a preferred embodiment, the inventive catalysts comprise, in addition to the metal of group VIII of the Periodic Table of the Elements, also at least one metal from group IB of the Periodic Table of the Elements. Particular preference is given in this context to silver.

In a particularly preferred embodiment, the inventive catalyst comprises palladium and silver.

The inventive catalyst may have any shapes, for example extrudates, hollow extrudates, tablets, rings, spherical particles or spheres. It is preferred when the inventive catalyst is in the form of an extrudate.

The metals may be present in pure metallic form, but also in the form of compounds, for example in the form of metal oxides. Under the operating conditions of a hydrogenation process, they are generally in the form of metals. Any oxides can be converted to metals in a manner known to those skilled in the art before the catalyst is used in a hydrogenation process, in or outside a hydrogenation reactor, for example by prereduction and, if necessary or advantageous for manipulations with the prereduced catalyst, subsequent surface passivation.

The content in the catalyst of metal or metals of group VIII of the Periodic Table, in particular palladium, is preferably at least 0.01% by weight, more preferably at least 0.1% by weight, in particular at least 0.15% by weight. This content is preferably at most 5% by weight, more preferably at most 1% by weight, in particular at most 0.6% by weight. Lower and higher contents are possible, but are normally economically unsatisfactory owing to too low an activity or excessively high raw material costs. In a particularly preferred embodiment, only one hydrogenating metal, in particular palladium, is used.

The ratio of the amounts of hydrogenation metal of group VIII of the Periodic Table of the Elements and additives or dopants is a parameter to be optimized in the individual case. The atomic ratio of metal of group VIII of the Periodic Table of the Elements, more preferably palladium, to the promoter, more preferably silver, is preferably 0.1-10, more preferably 2-7, in particular 2.5-6.

The oxidic support of the inventive hydrogenation catalyst is preferably alumina, more preferably in a mixture of δ-, θ- and α-alumina. The support may comprise, in addition to unavoidable impurities, other additives to a certain degree. For example, other inorganic oxides such as oxides or metals of groups IIA, IIIB, IVB, IIIA and IVA of the Periodic Table of the Elements may be present, in particular silicon dioxide, titanium dioxide, zirconium dioxide, zinc oxide, magnesium oxide, sodium oxide and calcium oxide. The maximum content in the support of such oxides other than alumina depends upon the oxide actually present, but should be determined in the individual case with reference to the x ray diffraction pattern of the hydrogenation catalyst, since a change in the structure is associated with a significant change in the x-ray diffraction diagram. In general, the content of such oxides other than alumina is below 50% by weight, preferably below 30% by weight, more preferably below 10% by weight. The degree of purity of the alumina is preferably higher than 99%.

To prepare the support, a suitable aluminum-containing raw material, preferably boehmite, is peptized with a peptizing agent such as water, dilute acid or dilute base. The acid used is, for example, a mineral acid, for instance nitric acid, or an organic acid, for instance formic acid. The base used is preferably an inorganic base, for instance ammonia. The acid or base is generally dissolved in water. The peptizing agents used are preferably water or dilute aqueous nitric acid. The concentration of the nonaqueous fraction in the peptizing agent is generally 0-10% by weight, preferably 0-7% by weight, more preferably 0-5% by weight. After the peptization, the support is shaped, dried and calcined.

Boehmite (γ-AlO(OH)) is a widely available commercial product, but may also be prepared in a known manner immediately before the actual support preparation by precipitating from a solution of an aluminum salt, for example aluminum nitrate, with a base, removing, washing, drying and calcining the precipitated solid. Advantageously, boehmite is used in the form of a powder. A suitable commercially available boehmite powder is, for example, Versal® 250 which is obtainable from UOP. The boehmite is treated with the peptizing agent by moistening and intensively mixing it with the peptizing agent, for example in a kneader, mixer or edge-runner mill. The peptization is continued until the composition is readily shapable. Subsequently, the composition is shaped to the desired shaped support bodies by means of customary methods, for example by extrusion, tableting or agglomeration. For the shaping, any known method is suitable. If necessary or advantageous, customary additives may be used. Examples of such additives are extruding or tableting assistants such as polyglycols or graphite.

It is also possible to add to the raw support material before the shaping additives which influence the pore structure of the support after the calcination in a known manner as burnout materials, for example polymers, fibrous materials, natural burnout materials such as nutshell meal, or other customary additives. Preference is given to using boehmite in a particle size distribution and to adding burnout materials which lead to a pore radius distribution of the finished support at which 50-90% by volume of the total pore volume is present in the form of pores having an average diameter in the range of from 0.01-0.1 μm and 10-50% by volume of the total pore volume in the form of pores having an average diameter in the range of from 0.1-1 μm The measures necessary for this purpose are known per se to those skilled in the art.

After the shaping, the shaped bodies are dried in a customary manner, generally at a temperature above 60° C., preferably above 80° C., more preferably above 100° C., in particular at a temperature in the range of from 120-300° C. The drying is continued until water present in shaped bodies has escaped essentially fully from the shaped bodies, which is generally the case after a few hours. Typical drying times are in the range from 1 to 30 hours and are dependent upon the drying temperature set, a higher temperature shortening the drying time. The drying may be accelerated further by employing a reduced pressure.

After the drying, the shaped bodies are converted to the finished support by calcination. The calcination temperature is generally in the range of 900-1150° C., preferably in the range of 1000-1120° C., more preferably in the range of 1050-1100° C. The calcination time is generally between 0.5 and 5 hours, preferably between 1 and 4 hours, more preferably between 1.5 and 3 hours. The calcination is effected in a customary furnace, for example in a rotary furnace, in a tunnel furnace, in a belt calciner or in a chamber furnace. The calcination may follow the drying directly without intermediate cooling of the shaped bodies.

The thus obtained inventive catalysts have a specific surface area (BET, Brunauer-Emmet-Teller, determined to DIN 66131 by nitrogen adsorption at 77 K) of 20-250 m²/g, preferably 50-150 m²/g, in particular 60-90 m²/g. The surface area may be varied by known methods, in particular use of finely divided or coarser starting materials, calcination time and calcination temperature. Like the BET surface area, the pore volume may also be varied in a known manner; in general, it is, determined by means of mercury porosimetry, in a range of 0.3-1.0 ml/g, preferably in a range of 0.4-0.9 ml/g, more preferably 0.5-0.8 ml/g.

After the calcination, the active composition and any further additives are deposited on the thus prepared support.

The support of the inventive catalyst is preferably characterized by the following x-ray diffraction diagram:

| Interplanar spacing ängstrøm [Å] | Angle 2-theta [°] | Relative intensity [%] |
|---|---|---|
| d = 4.552 | 19.483 | 5-15 |
| d = 2.857 | 31.278 | 35-50 |
| d = 2.730 | 32.775 | 65-80 |
| d = 2.449 | 36.671 | 45-55 |
| d = 2.317 | 38.842 | 35-45 |
| d = 2.260 | 39.861 | 35-45 |
| d = 2.022 | 44.790 | 45-65 |
| d = 1.910 | 47.570 | 30-40 |
| d = 1.798 | 50.720 | 10-25 |
| d = 1.543 | 59.915 | 25-35 |
| d = 1.511 | 61.307 | 0-35 |
| d = 1.489 | 62.289 | 20-30 |
| d = 1.455 | 63.926 | 25-35 |
| d = 1.387 | 67.446 | 100 |

This x-ray diffractogram is determined as described in EP 0 992 284 A2 on page 9, lines 6 to 9.

X-ray diffractograms are characteristic of the specific structure of the material analyzed. The structure of the inventive catalyst is defined sufficiently by the occurrence of the above-specified reflections. In addition to the above-specified characteristic reflections, one or more reflections may occur in any intensity in the x-ray diffraction diagram for the interplanar spacings 3.48; 2.55; 2.38; 2.09; 1.78; 1.74; 1.62; 1.60; 1.57; 1.42; 1.40 and/or 1.37, all in the unit [Å].

In addition, any other reflections may occur in the x-ray diffraction diagram of the inventive catalyst.

The active composition and any further additives may be deposited onto the thus obtained support of the inventive catalyst.

The metals, additives and/or dopants to be deposited onto the support may be applied to the support by any known process, for example by coating from the gas phase (chemical or physical vapor deposition) or saturating the support material in a solution which comprises the substances and/or compounds to be deposited.

The preferred method is the impregnation with a solution of the substances and/or compounds to be deposited which are converted to the substances to be deposited in the course of the further catalyst preparation. The substances to be deposited may be deposited individually and/or in portions, in a plurality of process steps or combined and fully in one process step. Preference is given to the combined deposition in one impregnation step. After the impregnation or after the individual impregnation steps, the supported catalyst is dried and converted to the ready-to-use catalyst by calcining and any other known aftertreatment methods, for example activation and subsequent surface passivation.

Impregnation processes for depositing active components, additives and/or dopants onto a support are known. In general, the support is impregnated with a solution of salts of the components to be deposited, the volume of the solution being such that the solution is taken up virtually fully by the pore volume of the support (incipient wetness method). The concentration of the salts in the solution is such that, after impregnation and conversion of the supported catalyst to the finished catalyst, the components to be deposited are present on the catalyst in the desired concentration. The salts are selected in such a way that they do not leave any troublesome residues in the course of the catalyst preparation or its later use. Usually, nitrates or ammonium salts are used.

In principle, all impregnation processes known to those skilled in the art are suitable for preparing the inventive catalyst.

However, preference is given to preparing the inventive catalyst with one stage impregnation of the support by the incipient wetness method of a nitric acid solution of the nitrates of the metals to be deposited.

In a particularly preferred embodiment, an impregnation solution is used which comprises palladium nitrate and nitrite together.

In addition, the metal of group IB of the Periodic Table of the Elements, preferably silver nitrate, is also present in the impregnation solution.

In general, the pH of the impregnation solution is at most 5, preferably at most 2, more preferably at most 1, in particular at most 0.5. The lower limit of the pH is generally 0.2, preferably 0.3, more preferably 0.5. A particularly preferred pH range is from 0.3 to 0.5.

After the impregnation, the impregnated support is dried in a customary manner, generally at a temperature above 60° C., preferably above 80° C., more preferably above 100° C., in particular at a temperature in the range of 120-300° C. The drying is continued until water present in the impregnated catalyst has escaped essentially fully, which is generally the case after a few hours. Typical drying times are in the range of 1-30 hours and depend upon the drying temperature set, a higher drying temperature shortening the drying time. The drying may be accelerated further by employing a reduced pressure.

In a particularly preferred embodiment of the process according to the invention, the impregnated catalyst is dried with simultaneous motion of the impregnated support material, for example in a rotary tube furnace.

In a particular embodiment of the present invention, the air stream used for drying is conducted through the rotary tube in countercurrent.

After the drying, the catalyst is prepared in a customary manner by calcination. This calcination serves essentially to convert the impregnated salts to the components to be deposited or precursors of such components and differs in this respect from the above-described calcination which serves to prepare the support material and the support structure. In the case of the impregnation of metal nitrates, the nitrates are decomposed substantially in the course of this calcination to metals and/or metal oxides which remain in the catalyst, and to nitrous gases which escape.

The calcination temperature is generally 200-900° C., preferably 280-800° C., more preferably 300-700° C. The calcination time is generally between 0.5 and 20 hours, preferably between 0.5 and 10 hours, more preferably between 0.5 and 5 hours. The calcination is effected in a customary furnace, for example in a rotary tube furnace, in a belt calciner or in a chamber furnace. The calcination may follow the drying directly without intermediate cooling of the supported and dried support.

In a particularly preferred embodiment of the process according to the invention, the drying and the calcination of the catalyst are combined in one rotary tube furnace.

After the calcination, the catalyst is in principle ready to use. If necessary or desired, it is activated by prereduction in a known manner before installation into the hydrogenation reactor and, if appropriate, also surface-passivated again.

In general, the hydrogenation catalyst is, however, usually not reduced until within the hydrogenation reactor itself. This is done in a way known to those skilled in the art by initial inertization with nitrogen or another inert gas. The reduction is carried out with a hydrogenous gas as a pure gas phase or under inert circulation. The temperature at which this prereduction is carried out is generally 5-200° C., preferably 20-150° C.

A regeneration of the inventive catalyst is also possible outside or inside the hydrogenation reactor at temperatures of from 15 to 500° C.

The present invention further provides the hydrogenation catalysts obtainable by this process.

The present invention further relates to the use of the inventive catalysts for hydrogenating unsaturated compounds and to corresponding hydrogenation processes.

The processes according to the invention for selective hydrogenation feature the use of the inventive catalyst. The inventive hydrogenation process is generally carried out just like the known heterogeneously catalyzed hydrogenation processes which serve the same purposes. They may be carried out as heterogeneously catalyzed gas phase processes in which both the hydrocarbon stream and the hydrogenation hydrogen are present in the gas phase or as heterogeneously catalyzed gas/liquid phase processes in which the hydrocarbon stream is present at least partly in the liquid phase and hydrogen is present in the gas phase and/or in dissolved form in the liquid phase. The parameters to be established, such as throughput of hydrocarbon stream, expressed in space velocity in the unit $[m^3/m^3(cat) \cdot h]$ or mass velocity $[t/m^3(cat) \cdot h]$, based on the catalyst volume, temperature and pressure, are selected analogously to the known processes. The inlet temperature is typically in the range from 0 to 100° C. and the pressure in the range from 2 to 50 bar. The hydrogenation may be carried out in one or more reaction stages, in which case an inventive catalyst is used in at least one reaction stage.

The amount of hydrogen used, based on the amount of hydrocarbon stream supplied, depends upon the content in the hydrocarbon stream of undesired unsaturated compounds and the type thereof. In general, the hydrogen is added in an amount of from 0.4 to 5 times the amount required stoichiometrically for full hydrogen conversion in the course of passage through the reactor. The hydrogenation of triple bonds normally proceeds more rapidly than that of conjugated double bonds and the latter in turn more rapidly than that of unconjugated double bonds. This allows a corresponding control of the process by means of the amount of hydrogen added. In special cases, for example when high isomerization of 1-butene to cis- or trans-2-butene is desired, it is also possible to use a higher hydrogen excess, for example a 10-fold hydrogen excess. The hydrogen may comprise inert gases, for example noble gases such as helium, neon or argon, nitrogen, carbon dioxide and/or lower alkanes such as methane, ethane, propane and/or butane. Such inert gases are present in the hydrogen preferably in a concentration of less than 30% by volume. Particular preference is given to the hydrogen being substantially free of carbon monoxide.

The processes may be carried out in one reactor or in a plurality of reactors connected in parallel or in series, in each case in single pass or in circulation mode. When the processes are carried out in the gas/liquid phase, the hydrocarbon stream is typically freed of gases in a separator after it has passed through a reactor and a portion of the resulting liquid is recycled into the reactor. The ratio between recycled hydrocarbon stream and that being fed into the reactor for the first time, known as the reflux ratio, is adjusted in such a way that the adiabatic temperature increase does not become too great under the other reaction conditions such as pressure, inlet temperature, throughput and amount of hydrogen.

Uses of the processes according to the invention are, for example, the hydrogenation of ethyne in C2 streams, in particular of propyne and/or propadiene to propene in C3 streams, in particular of 1,3-butadiene to butenes in C4 streams and/or of alkynes, dienes and styrene in C5+ streams (pyrolysis benzine).

Thus, the inventive catalysts are suitable, for example, for use in a process for selectively hydrogenating unsaturated hydrocarbons from alkene- and/or alkadiene-containing liquid hydrocarbon mixtures whose main constituents contain three carbon atoms in the molecule, wherein the inventive catalyst is contacted with the hydrocarbon stream, for example under the conditions described above.

Hydrogenation processes for such C3 streams are already known from the prior art. For instance, DE 37 09 328 A1 describes a trickle phase process for selectively hydrogenating highly unsaturated hydrocarbons. The process serves to very substantially and selectively remove highly unsaturated components from alkene-, alkadiene- and/or aromatics-containing liquid hydrocarbon mixtures whose main constituents contain at least three carbon atoms in the molecule. In this case, the hydrogenation is effected over a fixed bed supported palladium catalyst or a fixed bed catalyst system composed of from two to four supported palladium catalysts.

A disadvantage of this process using pure palladium catalysts is that the use of pure palladium catalysts leads readily to overhydrogenation and to green oil formation. This has the consequence of rapid carbonization and thus results in short lifetimes of the catalyst used.

In order to prevent this, the inventive catalyst which preferably contains silver is used in a hydrogenation process for hydrogenating C3 streams. This reduces the overhydrogenation and green oil formation. In addition, the palladium used has to be localized in a particular edge zone of the catalyst in order to have an adequate activity for the hydrogenation of the C3 streams. This is satisfied by the inventive catalysts which have a penetration depth of the palladium of up to 1000 μm.

The silver used is additionally distributed substantially homogeneously over the entire profile of the catalyst. This reduces or prevents green oil formation by the catalyst. This too is satisfied by the inventive catalysts which have silver substantially distributed virtually homogeneously over the whole extrudate cross section.

The process according to the invention for hydrogenating the C3 streams serves substantially for the selective hydrogenation of propyne and/or propadiene to propene present in these hydrocarbon mixtures with minimal formation of propane.

In a particularly preferred embodiment, the hydrogenation is effected in one stage.

Alternatively, the hydrogenation may also be carried out in two process stages. In that case, the thus obtained C3 stream has, before the particular hydrogenation stages, for example, the following contents:

| $C_3$ feed | $1^{st}$ stage | $2^{nd}$ stage |
|---|---|---|
| Propane | 1-20% | 1-20% |
| Propyne/propadiene (MAPD) | 2-6% | 0.1-0.2% |

-continued

| $C_3$ feed | $1^{st}$ stage | $2^{nd}$ stage |
|---|---|---|
| Propene | Remainder | Remainder |
| Further impurities having a content <1% (methane, C2 hydrocarbons, cyclopropane, C4 hydrocarbon, e.g. 1,3-butadiene, 1-butene, 2-butene (cis/trans)) | | |

The C3 hydrogenation is effected preferably with a predominantly liquid C3 phase and a hydrogen gas phase.

In this hydrogenation, the pressure is preferably from 9 to 30 bar g, more preferably from 10 to 25 bar g, in particular from 10 to 16 bar g. The inlet temperature is preferably from 0 to 50° C., more preferably from 0 to 40° C., in particular from 20 to 30° C. The temperature increase is preferably from 0 to 60° C., more preferably from 0 to 40° C., in particular from 0 to 5° C. The weight hourly space velocity (whsv) is preferably from 3 to 30 kg/l h, more preferably from 5 to 25 kg/l h, in particular from 8 to 15 kg/l h. The superficial velocity is preferably from 0.2 to 20 cm/s, more preferably from 0.5 to 10 cm/s, in particular from 1 to 5 cm/s. The ratio of hydrogen to methylacetylene and propadiene is preferably from 0.9 to 2, more preferably from 1.01 to 2.

In a preferred embodiment, the C3 hydrogenation is effected in one stage. Alternatively, a hydrogenation in two stages is also possible.

The reaction is effected in a manner known per se to those skilled in the art, for example adiabatically, with evaporative cooling or isothermally, preferably isothermally, and particular preference is given to using a coolant, for example ammonia, in the isothermal reaction.

The present invention further provides for the use of the inventive hydrogenation catalysts in processes for hydrogenating C4 streams.

Processes for hydrogenating C4 streams are known from the prior art. For instance, EP 0 523 482 B1 describes a process for selectively hydrogenating butadiene to butenes in the liquid or trickle phase over fixed bed supported noble metal catalysts. In this process, a butadiene-rich C4 stream having butadiene contents of 20-80% by weight, based on the C4 stream, is hydrogenated in two reaction zones connected in series in such a way that the hydrogenation product of the first reaction zone comprises 0.1-20% by weight and the hydrogenation product of the second reaction zone 0.005-1% by weight of residual butadiene based on the C4 stream.

The C4 hydrocarbon mixtures to be used in the present inventive hydrogenation are formed mainly in the course of steamcracking of mineral oil-derived hydrocarbons, for example naphtha. In addition to the main 1,3-butadiene component, these hydrocarbon mixtures may also comprise small amounts of compounds with cumulated double bonds and/or acetylenic triple bonds. The composition of the crude C4 cut from the steamcracker may vary within wide ranges (see table 1).

TABLE 1

Typical composition of a C4 cut of a steamcracker, reported in % by weight.

| $C_4$ feed sum | C3 traces | <1 |
|---|---|---|
| 1,3-butadiene | | 35-70 |
| isobutene | | 14-35 |
| 1-butene | | 5-22 |
| trans-2-butene | | 3-7 |
| cis-2-butene | | 2-6 |

TABLE 1-continued

Typical composition of a C4 cut of a steamcracker, reported in % by weight.

| $C_4$ feed sum | C3 traces | <1 |
|---|---|---|
| butane | | 1-12 |
| isobutane | | 0-10 |
| butenyne | (vinylacetylene) | 0.3-2 |
| 1-butyne | (ethylacetylene) | 0.1-0.5 |
| 1,2-butadiene | | 0-0.5 |
| sum | C5 traces | <1 |

The composition is essentially dependent upon the feedstock and the cleavage conditions of the steamcracker. Typically, the crude C4 cut comprises between 35-50% by weight of butadiene.

In principle, it is possible by the processes according to the invention or inventive catalysts to selectively hydrogenate all C4 cuts, however they have been obtained, having butadiene contents up to 80% by weight. Preference is given to using C4 streams which comprise 30-60% by weight of butadiene. Vinylacetylene and butynes are likewise hydrogenated selectively to butenes. n-Butane and isobutane emerge from the process according to the invention unchanged. Depending on the process conditions, isobutene may be hydrogenated undesirably at high hydrogenation severity to isobutane.

The process according to the invention is appropriately carried out in the liquid or trickle phase, and the hydrogen is distributed finely in the liquid C4 stream in a manner known per se. Preference is given to carrying out the selective hydrogenation of the butadiene in the trickle phase from the top downward with fixed bed hydrogenation catalysts. It is also possible to carry it out from the bottom upward.

In preferred embodiments, the process according to the invention for hydrogenating C4 streams is carried out in two or three stages.

The two reaction zones have to be separated from one another in such a way that hydrogen can be metered in and distributed finely between them. Preference is given to designing the reaction zones in the form of separate hydrogenation reactors. The hydrogen is added in one to two times the amount needed stoichiometrically for the calculated conversion (based on the overall process (all stages)); preference is given to adding the amount required stoichiometrically up to a 1.2-fold hydrogen excess.

The hydrogen used for the hydrogenation may comprise up to 30% by volume of inert gas, e.g. methane, without this significantly impairing the hydrogenation. The hydrogen used for the process according to the invention should preferably be CO-free; but small amounts of CO (<5 ppm) are not troublesome.

The reaction conditions in each of the reactors may be varied within wide ranges. For instance, the process according to the invention proceeds at a reactor inlet temperature of from 20 to 100° C., preferably from 30 to 90° C., the temperature increase being preferably from 10 to 60° C. The pressure is preferably from 5 to 50 bar g, more preferably from 5 to 30 bar. The liquid hourly space velocity (lhsv) based on the C4 feed is preferably from 1 to 30 $h^{-1}$, preferably from 2 to 15 $h^{-1}$. The fresh feed weight hourly space velocity (whsv) is preferably from 0.5 to 15 kg/1 h. The ratio of circulation stream to fresh feed is preferably from 2 to 20. The ratio of hydrogen to butadiene is preferably from 1 to 1.5.

Under these conditions, a maximum content of 1-butene is achieved at low exit content of 1,3-butadiene of preferably from 10 to 1000 ppm, and a high 1-butene selectivity is achieved. Thus, the 1-butene content in the hydrogenated C4 stream is preferably 30%, more preferably 40%, in particular 50% (after isobutene removal, remainder of isobutene: preferably from 0.5 to 4%, more preferably from 1 to 3%), while the ratio of 1-butene to 2-butene is preferably from 1.2 to 2.0, more preferably from 1.3 to 1.6.

When the hydrogenation of the C4 stream is effected in two stages, preference is given to using the inventive catalyst in the first reaction stage, in which case a 1-butene selectivity of preferably greater than 60% is achieved.

The process according to the invention has a series of advantages. The butadiene present in the feedstock is hydrogenated virtually quantitatively with very high selectivity. In spite of the very high butadiene conversion, a butene selectivity S of at least 96% is achieved in this process.

The hydrogenation is selective over a very wide range up to extremely high butadiene conversions. The isomerization of butene-1 to butene-2 is distinctly smaller than in the standard processes by virtue of the selection of the inventive catalyst in the first stage, and isobutene is substantially not converted to isobutane. No special purity requirements are made on the hydrogen, as long as no irreversible catalyst poisons such as lead or arsenic are present. The hydrogen metering may be controlled with automatic analytical processes.

Since the selectivity is retained even at relatively high reaction temperature, no complex cooling apparatus or plants for refrigeration are required. The heat removal is controlled in a simple manner via a sufficient amount of liquid recycle of hydrogenated product. A heat exchanger is disposed in the circulation stream.

In addition, no noticeable amounts of oligomerization products are formed in the process according to the invention.

The present invention is illustrated in detail with reference to the examples described below.

1. C3 Hydrogenation:

The catalysts are prepared by the incipient wetness method known to those skilled in the art.

The palladium content of the impregnation solution is adjusted to the particular value via the dilution of a palladium-containing stock solution in nitric acid to the particular value. In this dilution, the starting solution is a stock solution with about 11% palladium, present substantially as the nitrate, with a content of from 2 to 6% by weight of nitrite in the stock solution.

In the examples, catalyst support extrudates with a diameter of 3 mm are used.

1.1 Preparation of a Comparative Catalyst I $Al_2O_3$ extrudates having a surface area of 60-90 $m^2/g$ are impregnated with an impregnation solution comprising palladium nitrate and palladium nitrite which has been acidified with nitric acid to a pH of from 0.2 to 2. The moist extrudates are dried at 200° C. and calcined at 600° C. This affords a comparative catalyst I having 0.3% by weight of palladium.

The concentration of nitrite ions in the impregnation solution is 0.1%. Nitrate supplies the predominant portion of the anions.

1.2 Preparation of a Comparative Catalyst II

The comparative catalyst II is prepared analogously to the example for the preparation of the comparative catalyst I, except that the pH is less than 0.2 and the use of less palladium and more silver in the impregnation solution results in a catalyst having 0.2% by weight of palladium and 0.1% by weight of silver.

In this catalyst, the palladium is not present in a shell of up to 1000 μm, but rather is, like silver, distributed substantially homogeneously over the entire cross section of the catalyst.

1.3 Preparation of the Inventive Catalyst III

The inventive catalyst III is prepared analogously to the preparation of the comparative catalyst II (pH from 0.2 to 2). This results in a catalyst having 0.2% by weight of palladium and 0.1% by weight of silver.

1.4 Preparation of the Inventive Catalyst IV

The inventive catalyst IV is prepared analogously to the inventive catalyst III, except that a catalyst having 0.5% by weight of palladium and 0.1% by weight of silver is obtained by the use of more palladium nitrate and nitrite.

The thus prepared catalysts are used in the hydrogenation of a C3 stream. The hydrogenation takes place in one reactor. The reactor is equipped with:

- quantitatively controlled reactant supply,
- quantitatively controlled hydrogen supply,
- a tubular reactor (length 2 m, internal diameter 17.6 mm), with internal centered thermoelement (sleeve diameter 4 mm) and preheating zone (V2A spheres), free cross section: $2.31 \times 10^{-4}$ m$^2$,
- product separator for gas and liquid phase separation,
- gas outlet system with condenser,
- liquid circulation and
- liquid output system.

The input and output analyses are carried out with the aid of an online GC chromatograph.

The reduction proceeding in situ before the reaction proceeds under the following conditions: 120° C., 40 l (STP)/h of H$_2$, 5 bar g for 12 hours.

| Reactant | % by weight |
|---|---|
| Propane | 3.3 |
| Propene | 92.5 |
| Propadiene | 1.8 |
| Propyne | 2.3 |
| C4 sum | 0.1 |

The hydrogenation is carried out under the following conditions:
70 ml of catalyst
T$_{in}$=20° C.
whsv=19 kg/l$_{cat}$h
Circulation: reactant amount=2
Pressure=10-20 bar g
Purity of the H$_2$=100% (not restrictive)
At an MAPD conversion of 99%, the following are obtained:

| Catalyst | | I | II | III | IV |
|---|---|---|---|---|---|
| Propene selectivity | [%] | 68 | −11 | 72 | 72 |
| Green oil formation (C6) | [ppm] | 5000 | 2000 | 2000 | 2000 |

Propene selectivity: Δpropene/ΔMAPD where MAPD = methylacetylene plus propadiene

2. Hydrogenation of C4 Streams

The catalysts are prepared by the incipient wetness method known to those skilled in the art.

The palladium content of the impregnation solution for the catalysts I, III, IV and V is adjusted to the particular value via the dilution of a palladium-containing stock solution in nitric acid to the particular value. In this dilution, the starting solution is a stock solution with about 11% palladium, present substantially as the nitrate, with a content of from 2 to 6% by weight of nitrite in the stock solution.

In the examples, catalyst support extrudates with a diameter of 3 mm are used.

2.1 Preparation of an Inventive Catalyst I

Al$_2$O$_3$ extrudates having a surface area of 60-90 m$^2$/g are impregnated with an impregnation solution comprising palladium nitrate, palladium nitrite and silver nitrate which have been acidified to a pH of from 0.2 to 2 with nitric acid. The moist extrudates are dried at 200° C. and calcined at 600° C. A catalyst is obtained which contains 0.3% by weight of palladium and 0.1% by weight of silver, the weight ratio of palladium to silver being 3.

2.2 Preparation of a Comparative Catalyst II

The comparative catalyst II is prepared like the inventive catalyst I, except that a different palladium nitrate stock solution with 0.06% by weight of NO$_2^-$ instead of from 2 to 6% by weight of NO$_2^-$ is used. The finished impregnation solution consequently contains 0.0024% by weight of NO$_2^-$.

2.3 Preparation of a Comparative Catalyst II

The comparative catalyst III is prepared correspondingly to the inventive hydrogenation catalyst I, except that the silver was dispensed with.

2.4 Preparation of an Inventive Catalyst IV

The inventive hydrogenation catalyst IV is prepared correspondingly to the inventive hydrogenation catalyst I, except that the result is a catalyst which has a ratio of palladium to silver of 6 with 0.05% of silver.

2.5 Preparation of an Inventive Hydrogenation Catalyst V

The inventive hydrogenation catalyst V is prepared correspondingly to the inventive hydrogenation catalyst I, the weight ratio of palladium to silver being 3.5 and the proportion of silver being 0.085%.

The thus obtained catalysts are tested in a selective hydrogenation of a crude C4 cut.

The experiments are carried out in an experimental plant which is equipped with an electrically heatable fixed bed reactor of diameter 16 mm and length 2 m, a preheating zone, a separator, a condenser for the reactor effluent and a liquid circulation system. The amount of catalyst used is 200 ml. The crude C4 cut is metered in using a conveying pump and mixed at a mixing point with the hydrogen fed under quantitative control. In the separator, the reaction effluent is separated into gas and liquid phase. The majority of the liquid phase is fed back into the reactor in the circulation system. A smaller portion corresponding to the amount of the crude C4 cut fed to the reactor is removed continuously from the separator as product. The analyses are carried out by means of a gas chromatograph.

Before hydrocarbon is fed into the reactor for the first time, the catalysts are treated with hydrogen at 120° C. and 5 bar of pressure over 12 hours. Subsequently, the plant is charged with already selectively hydrogenated C4 cut, heated to 50° C. and taken into operation. After the operating conditions (pressure, temperature, throughput) have been attained, the crude C4 cut and hydrogen are fed in. The hydrogenation is effected at 50° C. under the following conditions:

whsv=5 kg/l$_{cat}$h
circulation: reactant=8
pressure=10-15 bar g
purity of the H$_2$=100% (not restrictive)
Overall butene selectivity=1-(Δ(n-butane)/Δ(1,3-butadiene))
1-butene selectivity=Δ(1-butene)/Δ(1,3-butadiene)

At a butadiene conversion of 99%, the results are:

|  |  | Reactant | 1 | 2 | 3 | 4 | 5 |
|---|---|---|---|---|---|---|---|
| 1,3-butadiene | [% by wt.] | 42.8 | 0.4 | 0.4 | 0.4 | 0.4 | 0.4 |
| 1-butene | [% by wt.] | 14.2 | 41.0 | 40.2 | 33.5 | 37.0 | 38.3 |
| trans-2-butene | [% by wt.] | 4.8 | 18.3 | 18.8 | 23.6 | 21.2 | 20.2 |
| cis-2-butene | [% by wt.] | 3.6 | 6.1 | 6.3 | 8.5 | 7.1 | 6.8 |
| isobutene | [% by wt.] | 25.2 | 25.2 | 25.2 | 25.2 | 25.2 | 25.2 |
| isobutane | [% by wt.] | 1.8 | 1.8 | 1.8 | 1.8 | 1.8 | 1.8 |
| n-butane | [% by wt.] | 6.3 | 6.6 | 6.7 | 6.7 | 6.7 | 6.7 |
| C4 acetylenes | [% by wt.] | 0.7 | <0.01 | <0.01 | <0.01 | <0.01 | <0.01 |
| Remainder = e.g. C3 and C5 + HC |  |  |  |  |  |  |  |
| Overall butene sel. | [%] |  | 99.3 | 99.1 | 99.1 | 99.1 | 99.1 |
| 1-butene sel. | [%] |  | 63.2 | 61.5 | 45.5 | 53.8 | 56.8 |

What is claimed is:

1. A process for preparing a catalyst which comprises at least one metal of Group VIII of the Periodic Table of the Elements as a hydrogenating metal and additionally a promoter metal of Groups VIII, IB, or IIB of the Periodic Table of the Elements on an oxidic support, wherein at least 80% of the metal of group VIII of the Periodic Table of the Elements is present in substantially homogeneous distribution in a layer between the surface of the catalyst and a penetration depth which corresponds to not more than 80% of the radius of the catalyst, calculated from the surface of the catalyst, and the promoter is present in substantially homogeneous distribution over the entire cross section of the catalyst, in which an oxidic support is impregnated with a solution consisting of nitrate and nitrite salts of metals of group VIII of the Periodic Table of the Elements, nitrates of the promoter metal, and nitric acid, and wherein the solution has been acidified with the nitric acid to have a pH of at most 5, dried and calcined.

2. The process according to claim 1, wherein the catalyst has a diameter of from 2.5 to 10 mm, and wherein at least 80% of the metal of group VIII of the Periodic Table of the Elements is present in substantially homogeneous distribution in a layer between the surface of the catalyst and a penetration depth of not more than 1000 µm, calculated from the surface of the catalyst, and the promoter metal is present in substantially homogeneous distribution over the entire cross section of the catalyst.

3. The process according to claim 1, wherein the oxidic support is alumina.

4. The process according to claim 1, wherein the oxidic support is alumina in a mixture of δ-, θ- and α-alumina.

5. The process according to claim 1, wherein the metal of group VIII of the Periodic Table of the Elements is palladium.

6. The process according to claim 1, wherein the content of metal of group VIII of the Periodic Table is from 0.05 to 5% by weight based on the total weight of the catalyst.

7. The process according to claim 1, wherein the promoter is a metal of group IB of the Periodic Table of the Elements.

8. The process according to claim 7, wherein the metal of group IB of the Periodic Table of the Elements is silver.

9. The process according to claim 7, wherein the atom ratio between the metal of group VIII of the Periodic Table of the Elements to the metal of group IB of the Periodic Table of the Elements is from 0.1 to 10.

10. The process according to claim 1, wherein the catalyst is dried under motion in a rotary tube.

11. The process according to claim 1, wherein the drying is effected with an air stream as a countercurrent.

12. The process according to claim 1, wherein the drying and the calcination are combined in one rotary tube.

13. The process according to claim 1, wherein the catalyst is reduced outside or inside a hydrogenation reactor at temperatures of from 0 to 200° C.

14. The process according to claim 1, wherein the catalyst is regenerated outside or inside a hydrogenation reactor at temperatures of from 15 to 500° C.

15. A catalyst obtained by the process according to claim 1.

16. A method for hydrogenating unsaturated compounds comprising hydrogenating an unsaturated compound with the catalyst according to claim 15.

17. The method according to claim 16, wherein propyne and/or propadiene in C3 streams are hydrogenated to propene.

18. The method according to claim 16, wherein 1,3-butadiene in C4 streams is hydrogenated to butenes.

19. A process for selectively hydrogenating unsaturated compounds in the gas phase or mixed gas/liquid phase at inlet temperatures of from 0 to 100° C. and pressures in the range from 5 to 50 bar, carrying out the selective hydrogenation in one or more reaction stages and contacting the catalyst according to claim 15 in at least one reaction stage.

20. The process according to claim 19, wherein propyne and/or propadiene in C3 streams are hydrogenated to propene.

21. The process according to claim 19, wherein ethyne in C2 streams is hydrogenated.

22. The process according to claim 19, wherein alkynes, dienes and/or styrene in C5+ streams are hydrogenated.

23. The process according to claim 19, wherein 1,3-butadiene in C4 streams is hydrogenated to butenes.

24. The process according to claim 23, wherein the hydrogenation is carried out in two reaction stages and the catalyst according to claim 15 is contacted in the first stage.

25. The process according to claim 23, wherein a 1-butene selectivity of greater than 60% is achieved in the first reaction stage.

26. The process according to claim 1, wherein the metal of group VIII of the Periodic Table of the Elements is palladium and wherein the promoter is silver.

* * * * *